United States Patent
Bountra et al.

(10) Patent No.: US 7,390,817 B2
(45) Date of Patent: Jun. 24, 2008

(54) COMBINATIONS OF A VANILLOID ANTAGONIST AND AN NSAID FOR THE TREATMENT OF PAIN

(75) Inventors: Charanjit Bountra, Harlow (GB); John Beresford Davis, Harlow (GB); Harshad Kantilal Rami, Harlow (GB); Mervyn Thompson, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 409 days.

(21) Appl. No.: 10/540,100

(22) PCT Filed: Dec. 17, 2003

(86) PCT No.: PCT/EP03/14776

§ 371 (c)(1),
(2), (4) Date: Jun. 20, 2005

(87) PCT Pub. No.: WO2004/056394

PCT Pub. Date: Jul. 8, 2004

(65) Prior Publication Data

US 2006/0093687 A1    May 4, 2006

(30) Foreign Application Priority Data

Dec. 20, 2002  (GB) .................................. 0229808.1

(51) Int. Cl.
*A61K 31/44*   (2006.01)
*A01N 43/42*   (2006.01)
(52) U.S. Cl. ........................................ 514/279; 514/290
(58) Field of Classification Search ...................... None
See application file for complete search history.

(56) References Cited

U.S. PATENT DOCUMENTS

| 6,048,855 A | 4/2000 | Breton et al. |
| 2004/0138454 A1* | 7/2004 | Culshaw et al. ............. 544/279 |

FOREIGN PATENT DOCUMENTS

| WO | WO/0146194 | 6/2001 |
| WO | WO/0208221 | 1/2002 |
| WO | WO/02076946 | 10/2002 |
| WO | WO/03022809 | 3/2003 |
| WO | WO/03062209 | 7/2003 |

* cited by examiner

*Primary Examiner*—Sreeni Padmanabhan
*Assistant Examiner*—Samira Jean-Louis
(74) *Attorney, Agent, or Firm*—Steven Venetianer; William Marjarian; Reid S. Willis

(57) ABSTRACT

A method of treating conditions associated with pain and alleviating the symptoms associated therewith which comprises administering to a mammal, including man, a vanilloid VR-1 antagonist or a pharmaceutically acceptable derivative thereof and an NSAID or a pharmaceutically acceptable derivative thereof, wherein said VR-1 antagonist or said NSAID may optionally be administered as a sub-maximal amount.

2 Claims, No Drawings

COMBINATIONS OF A VANILLOID ANTAGONIST AND AN NSAID FOR THE TREATMENT OF PAIN

This application claims the benefit of International Application No. PCT/EP2003/014776, filed 17 Dec. 2003

The present invention relates to the treatment of conditions associated with pain including acute pain, chronic pain, inflammatory pain, neuropathic pain and pain associated with migraine, tension headaches, cluster headaches and functional bowel disorder. In particular it relates to the use of a vanilloid receptor (VR-1) antagonist in conjunction with a non-steroidal anti-inflamatory drug (NSAID), such as a COX-2 inhibitor.

A variety of compounds which are antagonists of the vanilloid VR-1 receptor have been described in the art. These include compounds described in co-pending GB Patent Applications GB 0303464.2, GB 0305291.7, GB 0305290.9, GB 0305165.3, GB 0305426.9, GB 0305285.9, GB 0305163.8 and GB 0316554.5 (Glaxo Group Ltd); co-pending International Patent Application Number PCT/EP03/10262 (Glaxo Group Ltd); and published International Patent Application, Publication Numbers WO 02/072536, WO 02/090326, WO 03/022809, WO 03/053945 and WO 03/068749 (Glaxo Group Ltd), WO 02/08221, WO 03/062209 (Neurogen Corporation US), WO 02/16317, WO 02/16318, WO 02/16319 (Pacific Corporation), WO 02/30956 (Diverdrugs ES), WO 02/076946 (Novartis AG), WO 03/049702 (Amgen Inc), WO 03/070247 (Abbott Laboratories), WO 03/066595, WO 03/074520 (Euro-Celtique S. A.), WO 03/014064, WO 03/055484, WO 03/095420 (Bayer Aktiengellschaft) and WO 03/080578 (Merck Sharpe & Dohme Limited). The aforementioned patent applications are incorporated herein by reference as if each individual application were specifically and individually indicated to be incorporated by reference herein as though fully set forth.

International Patent Application, Publication Number WO 021072536 (Glaxo Group Ltd) discloses compounds of formula (1):

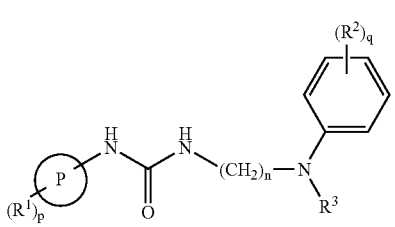

or a pharmaceutically acceptable salt thereof, or a solvate thereof, wherein, wherein, P is phenyl or naphthyl;

$R^1$ is halogen, alkyl, $CF_3$, hydroxy, alkyloxy, CN, $OCF_3$, alkylthio, alkylsulfinyl, alkylsulfonyl, nitro, amino, mono- or dialkylamino or C(O)alkyl;

p is 0, 1, 2 or 3;

n is 2, 3, 4, 5 or 6;

$R^2$ is halogen, alkyl, $CF_3$, alkoxy, CN, nitro, aryl, $OCF_3$, C(O)alkyl, amino, mono- or dialkylamino;

q is 0, 1, 2 or 3; and $R^3$ is hydrogen, alkyl or arylalkyl.

International Patent Application, Publication Number WO 02/090326 (Glaxo Group Ltd) discloses compounds of formula (2):

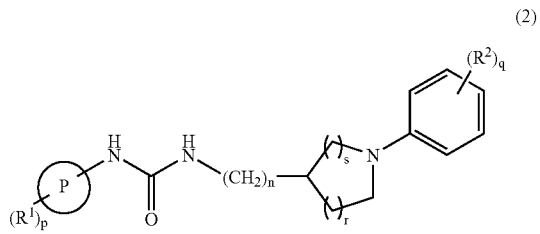

or a pharmaceutically acceptable salt thereof, or a solvate thereof, wherein, wherein, P is phenyl or naphthyl;

$R^2$ is halogen, $C_{1-6}$alkyl, $CF_3$, $C_{1-6}$alkoxy, CN, nitro, aryl, $OCF_3$, $C(O)C_{1-6}$alkyl, amino, mono- or di-$C_{1-6}$alkylamino;

$R^1$ and $R^2$ are independently selected from —H, -halo, —CN, —$NO_2$, —OH, —$CF_3$, —$OCF_3$, —$NR^4R^5$, —$S(O)_mR^6$, —$S(O)_2NR^4R^5$, —$OS(O)_2R^6$, —$OS(O)_2CF_3$, alkyl, cycloalkyl, alkoxy, —$O(CH_2)_nNR^4R^5$, —$C(O)CF_3$, —C(O)alkyl, —C(O)cycloalkyl, —C(O)alkylaryl, —C(O)aryl, —$C(O)(CH_2)_nOR^6$, —$C(O)(CH_2)_nNR^4R^5$, —C(O)Oalkyl, —$C(O)NR^4R^5$, —$(CH_2)_nC(O)$Oalkyl, —$(CH_2)_nOC(O)R^6$, —$(CH_2)_nOR^6$, —$(CH_2)_nNR^4R^5$, —$(CH_2)_nC(O)NR^4R^5$, —$(CH_2)_nN(R^4)C(O)R^6$, —$(CH_2)_nS(O)_2NR^4R^5$, —$(CH_2)_nN(R^4)S(O)_2R^6$, —ZAr, arylalkyl-, arylalkoxy-, cycloalkylalkyl-, cycloalkylalkoxy-, $R^6S(O)_2C_{1-6}$alkyl-, $R^6S(O)_2C_{1-6}$alkoxy-, $R^6S(O)_2N(R^4)$—, $R^6C(O)N(R^4)$—, $R^6S(O)_2N(R^4)$ $C_{1-6}$alkyl-, $R^6C(O)N(R^4)C_{1-6}$alkyl- or $R_6C(O)C_{1-6}$alkyl;

Ar represents an optionally substituted phenyl ring or an optionally substituted 5- or 6-membered aromatic heterocyclic ring and Z represents a bond, O, S, —$N(R^4)$ or $CH_2$;

$R^4$ and $R^5$ may be the same or different and represent H or alkyl or $R^4$ and $R^5$ together with the atoms to which they are attached form an optionally substituted, saturated ring having 3 to 6 atoms optionally comprising a further nitrogen atom and/or a moiety $NR^6$;

$R^6$ is $C_{1-6}$alkyl or aryl;

q is 0, 1, 2 or 3;

n is 0, 1, 2 or 3;

p is and q are independently 0, 1, 2 or 3 and when p is 2 or 3 the groups $R^1$ can be the same or different;

q is 0, 1, 2 or 3 and when q is 2 or 3 the groups $R^2$ can be the same or different;

r is 1, 2 or 3; and s is 0, 1 or 2;

and provided that the compound of formula (I) is not 1-(1-phenyl-3-pyrrolidinyl)-3-phenyl urea or 1-(1-phenyl-3-pyrrolidinyl)-3-(4-methoxyphenyl)urea.

International Patent Application, Publication Number WO 03/022809 (Glaxo Group Ltd) discloses certain compounds of formula (3):

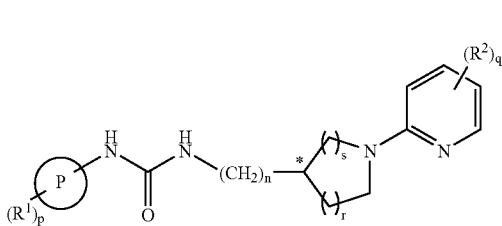

(3)

or a pharmaceutically acceptable salt thereof, or a solvate thereof, wherein,
P and P' are independently selected from aryl and heteroaryl;
$R^1$ and $R^2$ are independently selected from —H, halo, alkyl, alkoxy, cycloalkyl, aralkyl, aralkoxy, cycloalkylalkyl, cycloalkylalkoxy, —CN, —NO$_2$, —OH, —OCF$_3$, —CF$_3$, —NR$^4$R$^5$, —S(O)$_m$R$^6$, —S(O)$_2$NR$^4$R$^5$, —OS(O)$_2$R$^6$, —OS(O)$_2$CF$_3$, —O(CH$_2$)$_x$NR$^4$R$^5$, —C(O)CF$_3$, —C(O)alkyl, —C(O)cycloalkyl, —C(O)aralkyl, —C(O)Ar, —C(O)(CH$_2$)$_x$OR$^6$, —C(O)(CH$_2$)$_x$NR$^4$R$^5$, —C(O)alkoxy, —C(O)NR$^4$R$^5$, —(CH$_2$)$_x$C(O)alkoxy, —(CH$_2$)$_x$OC(O)R$^6$, —(CH$_2$)$_x$OR$^6$, —(CH$_2$)$_x$R$^4$R$^5$, —(CH$_2$)$_x$C(O)NR$^4$R$^5$, —(CH$_2$)$_x$N(R$^4$)C(O)R$^6$, —(CH$_2$)$_x$S(O)$_2$NR$^4$R$^5$, —(CH$_2$)$_x$N(R$^4$)S(O)$_2$R$^6$, —ZAr, —(CH$_2$)$_x$S(O)$_2$R$^6$, —(OCH$_2$)$_x$S(O)$_2$R$^6$, —N(R$^4$)S(O)$_2$R$^6$, —N(R$^4$)C(O)R$^6$, —(CH$_2$)$_x$N(R$^4$)S(O)$_2$R$^6$, —(CH$^2$)$_x$N(R$^4$)C(O)R$^6$ or —(CH$_2$)$_x$C(O)alkyl;
$R^4$ and $R^5$ may be the same or different and represent H or alkyl or $R^4$ and $R^5$ together with the atoms to which they are attached form a $C_{3-6}$azacycloalkane, $C_{3-6}$(2-oxo)azacycloalkane ring or $C_{5-8}$ polymethylene chain optionally interrupted by heteroatoms such as O or —NR$^7$;
Z is O, S or NR$^7$;
$R^6$ is alkyl or aryl;
$R^7$ is hydrogen, alkyl or aryl;
m is 1 or 2;
n is 0, 1, 2 or 3;
p and q are independently 0, 1, 2, or 3 or 4;
r is 1, 2 or 3;
s is 0, 1 or 2; and
x is 0, 1, 2, 3, 4, 5 or 6
(* indicates a chiral carbon atom).

International Patent Application, Publication Number WO 03/053945 (Glaxo Group Ltd) discloses compounds of formula (4):

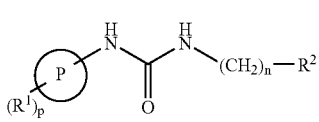

(4)

or a pharmaceutically acceptable salt thereof, or a solvate thereof, wherein,
P is phenyl, naphthyl or heterocyclyl;
$R^1$ is selected from —H, halo, alkyl, alkoxy, cycloalkyl, aralkyl, aralkoxy, cycloalkylalkyl, cycloalkylalkoxy, —CN, —NO$_2$, —OH, —OCF$_3$, —CF$_3$, —NR$^5$R$^6$, —S(O)$_m$R$^7$, —S(O)$_2$NR$^5$R$^6$, —OS(O)$_2$R$^7$, —OS(O)$_2$CF$_3$, —O(CH$_2$)$_x$NR$^5$R$^6$, —C(O)CF$_3$, —C(O)alkyl, —C(O)cycloalkyl, —C(O)aralkyl, —C(O)Ar, —C(O)(CH$_2$)$_x$OR$^7$, —C(O)(CH$_2$)$_x$NR$^5$R$^6$, —C(O)alkoxy, —C(O)NR$^5$R$^6$, —(CH$_2$)$_x$C(O)alkoxy, —(CH$_2$)$_x$OC(O)R$^7$, —(CH$_2$)$_x$OR$^7$, —(CH$_2$)$_x$R$^5$R$^6$, —(CH$_2$)$_x$C(O)NR$^5$R$^6$, —(CH$_2$)$_x$N(R$^5$)C(O)R$^7$, —(CH$_2$)$_x$S(O)$_2$NR$^5$R$^6$, —(CH$_2$)$_x$N(R$^5$)S(O)$_2$R$^7$, —ZAr, —(CH$_2$)$_x$S(O)$_2$R$^7$, —(OCH$_2$)$_x$S(O)$_2$R$^7$, —N(R$^5$)S(O)$_2$R$^7$, —N(R$^5$)C(O)R$^7$, —(CH$_2$)$_x$N(R$^5$)S(O)$_2$R$^7$, —(CH$^2$)$_x$N(R$^5$)C(O)R$^7$ or —(CH$_2$)$_x$C(O)alkyl;
$R^2$ is the group:

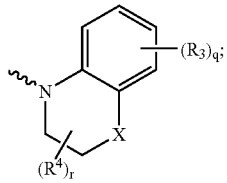

X is a bond, C, O or NR$^8$;
$R^3$ is selected from —H, halo, alkyl, alkoxy, cycloalkyl, aryl, aralkyl, aralkoxy, cycloalkylalkyl, cycloalkylalkoxy, —CN, —NO$_2$, —OH, —OCF$_3$, —CF$_3$, —NR$^5$R$^6$, —S(O)$_m$R$^7$, —S(O)$_2$NR$^5$R$^6$, —OS(O)$_2$R$^7$, —OS(O)$_2$CF$_3$, —O(CH$_2$)$_x$NR$^5$R$^6$, —C(O)CF$_3$, —C(O)alkyl, —C(O)cycloalkyl, —C(O)aralkyl, —C(O)Ar, —C(O)(CH$_2$)$_x$OR$^7$— C(O)(CH$_2$)$_x$NR$^5$R$^6$, —C(O)alkoxy, —C(O)NR$^5$R$^6$, —(CH$_2$)$_x$C(O)alkoxy, —(CH$_2$)$_x$OC(O)R$^7$, —(CH$_2$)$_x$OR$^7$, —(CH$_2$)$_x$R$^5$R$^6$, —(CH$_2$)$_x$C(O)NR$^5$R$^6$, —(CH$_2$)$_x$N(R$^5$)C(O)R$^7$, —(CH$_2$)$_x$S(O)$_2$NR$^5$R$^6$, —(CH$_2$)$_x$N(R$^5$)S(O)$_2$R$^7$, —ZAr, —(CH$_2$)$_x$S(O)$_2$R$^7$, —(OCH$_2$)$_x$S(O)$_2$R$^7$, —N(R$^5$)S(O)$_2$R$^7$, —N(R$^5$)C(O)R$^7$, —(CH$_2$)$_x$N(R$^5$)S(O)$_2$R$^7$, —(CH$^2$)$_x$N(R$^5$)C(O)R$^7$ or —(CH$_2$)$_x$C(O)alkyl;
$R^4$ is hydrogen or alkyl;
$R^5$ and $R^6$ may be the same or different and represent H or alkyl or $R^5$ and $R^6$ together with the atoms to which they are attached form a $C_{3-6}$azacycloalkane, $C_{3-6}$(2-oxo)azacycloalkane ring or $C_{5-8}$ polymethylene chain optionally interrupted by heteroatoms such as O or —NR$^8$;
Z is O, S or NR$^8$;
$R^7$ is alkyl or aryl;
$R^8$ is hydrogen, alkyl or aryl;
n is 2, 3, 4, 5 or 6;
p is 0, 1, 2, 3 or 4;
q is 0, 1, 2 or 3;
r is 0, 1 or 2; and
x is 0, 1, 2, 3, 4, 5 or 6.

International Patent Application, Publication Number WO 03/068749 (Glaxo Group Ltd) discloses certain compounds of formula (5):

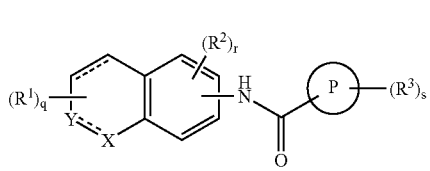

(5)

or a pharmaceutically acceptable salt thereof, or a solvate thereof, wherein,
P is selected from phenyl, heteroaryl or heterocyclyl;
$R^1$ and $R^2$ are independently selected from —H, halo, alkyl, alkoxy, cycloalkyl, aralkyl, aralkoxy, cycloalkylalkyl, cycloalkylalkoxy, —CN, —NO$_2$, —OH, =O, —OCF$_3$, —CF₃, —NR⁴R⁵, —S(O)ₘR⁶, —S(O)₂NR⁴R⁵, —OS(O)₂R⁶, —OS(O)₂CF₃, —O(CH₂)ₙNR⁴R⁵, —C(O) CF₃, —C(O)alkyl, —C(O)cycloalkyl, —C(O)aralkyl, —C(O)Ar, —C(O)(CH₂)ₙOR⁶, —C(O)(CH₂)ₙNR⁴R⁵, —C(O)alkoxy, —C(O)NR⁴R⁵, —(CH₂)ₙC(O)alkoxy, —(CH₂)ₙOC(O)R⁶, —O(CH₂)ₙOR⁶, —(CH₂)ₙOR⁶, —(CH₂)ₙR⁴R⁵, —(CH₂)ₙC(O)NR⁴R⁵, —(CH₂)ₙN(R⁴)C (O)R⁶, —(CH₂)ₙS(O)₂NR⁴R⁵, —(CH₂)ₙN(R⁴)S(O)₂R⁶, —ZAr, —(CH₂)ₙS(O)₂R⁶, —(OCH₂)ₙS(O)₂R⁶, —N(R⁴) S(O)₂R⁶, —N(R⁴)C(O)R⁶, —(CH₂)ₙN(R⁴)S(O)₂R⁶, —(CH²)ₙN(R⁴)C(O)R⁶ or —(CH₂)ₙC(O)alkyl;

R³ is selected from —H, alkyl, alkoxy, —CF₃, halo, —O(CH₂)ₙOR⁶, O(CH₂)ₙNR⁴R⁵, phenyl, cyclohexyl, benzo[1,3]dioxolyl, morpholinyl, pyridyl, pyrimidinyl, pyrazinyl, piperazinyl, piperidinyl, pyridizinyl, thienyl, furyl, pyrazolyl, pyrrolyl, triazolyl, indanyl, imidazolyl, oxazolyl, thiazolyl, oxadiazolyl, isothiazolyl, isoxazolyl or thiadiazolyl; wherein said alkyl, alkoxy, phenyl, cyclohexyl, benzo[1,3]dioxolyl, morpholinyl, pyridyl, pyrimidinyl, pyrazinyl, piperazinyl, piperidinyl, pyridizinyl, thienyl, furyl, pyrazolyl, pyrrolyl, triazolyl, indanyl, imidazolyl, oxazolyl, thiazolyl, oxadiazolyl, isothiazolyl, isoxazolyl and thiadiazolyl groups each of which may be may be optionally substituted by one or more groups, which may be the same or different, selected from R²;

R⁴ and R⁵ may be the same or different and represent —H or alkyl or together R⁴ and R⁵ together with the nitrogen atom to which they are attached form a heterocyclic ring; forms part of a $C_{3-6}$azacycloalkane, $C_{3-6}$(2-oxo)azacycloalkane ring or $C_{5-8}$polymethylene chain optionally interrupted by heteroatoms such as O or NR⁷;

R⁶ is —H, alkyl or aryl;

R⁷ is —H, alkyl or aryl;

R⁸ is selected from —H, alkyl, hydroxyalkyl, alkoxy, cycloalkyl, aralkyl, alkoxyalkyl, aralkoxy, cycloalkylalkyl, cycloalkylalkoxy, heterocyclylalkyl, —S(O)ₘR⁶, —C(O) CF₃, —C(O)alkyl, —C(O)cycloalkyl, —C(O)aralkyl, —C(O)Ar, —C(O)(CH₂)ₙOR⁶, —C(O)(CH₂)ₙNR⁴R⁵, —C(O)alkoxy, —C(O)NR⁴R⁵, —(CH₂)ₙC(O)alkoxy, —(CH₂)ₙOC(O)R⁶, —(CH₂)ₙOR⁶, —(CH₂)ₙR⁴R⁵, —(CH₂)ₙC(O)NR⁴R⁵, —(CH₂)ₙN(R⁴)C(O)R⁶, —(CH₂)ₙS(O)₂NR⁴R⁵, —(CH₂)ₙN(R⁴)S(O)₂R⁶, —(CH₂)ₙS(O)₂R⁶, —(CH₂)ₙN(R⁴)S(O)₂R⁶, —(CH²)ₙN (R⁴)C(O)R⁶ or —(CH₂)ₙC(O)alkyl; or where X is NR⁸ and Y is C(R⁹)₂, R⁸ may combine with R¹ to form a benzoquinuclidine group, P;

R⁹ is —H or R¹;

Ar is aryl or heterocyclylheteroaryl, each of which may be optionally substituted by R²;

Z is a bond, O, S, NR⁷ or CH₂;

m is 0, 1 or 2;

n is an integer value from 1 to 6;

q and r are independently selected from 0, 1, 2 or 3;

s is 0, 1, 2 or 3; and

X and Y are selected from the following combinations:

| X | Y |
|---|---|
| N | CR⁹H |
| NR⁸ | C(R⁹)H₂ |
| CR⁹H | N |
| C(R⁹)H₂ | NR⁸ |

X and Y are independently selected from CH or N, with the proviso that X and Y are not both CH or N.

International Patent Application, Publication Number PCT/EP03/10262 (Glaxo Group Ltd) discloses certain compounds of formula (6):

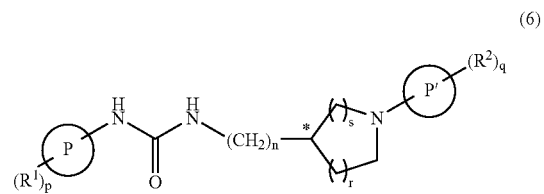

(6)

or a pharmaceutically acceptable salt thereof, or a solvate thereof, wherein,

P is selected from cinnolinyl, phenyl, quinazolinyl, quinolinyl or iso-quinolinyl;

P' is selected from pyrazidinyl, pyridinyl, pyrimidinyl or iso-quinolinyl;

R¹ and R² are independently selected from —H, halo, alkyl, alkoxy, cycloalkyl, aralkyl, aralkoxy, cycloalkylalkyl, cycloalkylalkoxy, —CN, —NO₂, —OH, —OCF₃, —CF₃, —NR⁴R⁵, —S(O)ₘR⁶, —S(O)₂NR⁴R⁵, —OS(O)₂R⁶, —OS(O)₂CF₃, —O(CH₂)ₓNR⁴R⁵, —C(O)CF₃, —C(O) alkyl, —C(O)cycloalkyl, —C(O)aralkyl, —C(O)Ar, —C(O)(CH₂)ₓOR⁶, —C(O)(CH₂)ₓNR⁴R⁵, —C(O) alkoxy, —C(O)NR⁴R⁵, —(CH₂)ₓC(O)alkoxy, —(CH₂)ₓOC(O)R⁶, —(CH₂)ₓOR⁶, —(CH₂)ₓR⁴R⁵, —(CH₂)ₓC(O)NR⁴R⁵, —(CH₂)ₓN(R⁴)C(O)R⁶, —(CH₂)ₓS(O)₂NR⁴R⁵, —(CH₂)ₓN(R⁴)S(O)₂R⁶, —ZAr, —(CH₂)ₓS(O)₂R⁶, —(OCH₂)ₓS(O)₂R⁶, —N(R⁴)S(O)₂R⁶, —N(R⁴)C(O)R⁶, —(CH₂)ₓN(R⁴)S(O)₂R⁶, —(CH²)ₓN (R⁴)C(O)R⁶ or —(CH₂)ₓC(O)alkyl;

R⁴ and R⁵ may be the same or different and represent H or alkyl or R⁴ and R⁵ together with the atoms to which they are attached form a $C_{3-6}$azacycloalkane, $C_{3-6}$(2-oxo)azacycloalkane ring or $C_{5-8}$ polymethylene chain optionally interrupted by heteroatoms such as O or —NR⁷.

Z is O, S or NR⁷;

R⁶ is alkyl or aryl;

R⁷ is hydrogen, alkyl or aryl;

m is 1 or 2;

n is 0, 1, 2 or 3;

p and q are independently 0, 1, 2, 3 or 4;

r is 1, 2 or 3;

s is 0, 1 or 2; and x is 0, 1, 2, 3, 4, 5 or 6.

GB Patent Application No. 0303464.2 (Glaxo Group Ltd) discloses compounds of formula (7):

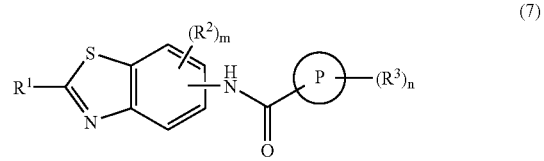

(7)

or a pharmaceutically acceptable salt thereof, or a solvate thereof, wherein,

P is aryl or heteroaryl;

R¹ is —H, alkyl, heterocyclyl wherein said heterocyclyl may be optionally substituted by alkyl; heterocyclylalkyl, —(CH₂)ₓO(CH₂)ₓOR⁴, —(CH₂)ₓO(CH₂)ₓ-heterocyclyl, —NR⁴(CH₂)ₓOR⁴ or —NR⁴(CH₂)ₓ-heterocyclyl;

$R^2$ is halo;

$R^3$ is halo, alkyl, alkoxy, cycloalkyl, aryl wherein said aryl group may be optionally substituted by one or more halo atoms; aralkyl, aralkoxy, cycloalkylalkyl, cycloalkylalkoxy, —CN, —$NO_2$, —OH, —$OCF_3$, —$CF_3$, —$NR^4R^5$, —$S(O)_mR^6$, —$S(O)_2NR^4R^5$, —$OS(O)_2R^6$, —$O(CH_2)_xNR^4R^5$, —$O(CH_2)_xOR^4$, —$C(O)CF_3$, —C(O)alkyl, —C(O)cycloalkyl, —C(O)aralkyl, —C(O)Ar, —$C(O)(CH_2)_xOR^4$, —$C(O)(CH_2)_xNR^4R^5$, —C(O)alkoxy, —$C(O)NR^4R^5$, —$(CH_2)_xC(O)$alkoxy, —$(CH_2)_xOC(O)R^4$, —$(CH_2)_xOR^4$, —$(CH_2)_xNR^4R^5$, —$(CH_2)_xC(O)NR^4R^5$, —$(CH_2)_xN(R^4)C(O)R^4$, —$(CH_2)_xS(O)_2NR^4R^5$, —$(CH_2)_xN(R^4)S(O)_2R^6$, —ZAr, —$(CH_2)_xS(O)_mR^6$, —$O(CH_2)_xS(O)_mR^6$, —$N(R^4)S(O)_2R^6$, —$N(R^4)C(O)R^4$, —$(CH_2)_xN(R^4)S(O)_2R^6$, —$(CH_2)_xN(R^4)C(O)R^4$ or —$(CH_2)_xC(O)$alkyl;

$R^4$ and $R^5$ may be the same or different and represent —H, alkyl or aryl or $R^4$ and $R^5$ together with the nitrogen atom to which they are attached form a heterocyclic ring;

$R^6$ is alkyl or aryl;

$R^7$ is —H, alkyl or aryl;

Ar is aryl or heteroaryl;

x is 0, 1, 2, 3, 4, 5 or 6;

Z is a bond, O, S, $NR^7$ or $CH_2$;

m is 0, 1 or 2; and n is an integer value from 1 to 6.

GB Patent Application No. 0305291.7 (Glaxo Group Ltd) discloses compounds of formula (8):

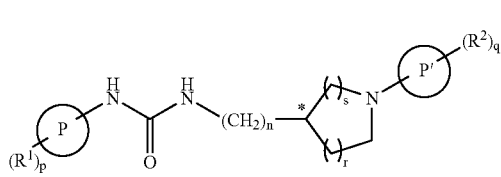

(8)

or a pharmaceutically acceptable salt thereof, or a solvate thereof, wherein:

P and P' are independently selected from aryl and heteroaryl;

$R^1$ and $R^2$ are independently selected from —H, halo, alkyl, alkoxy, cycloalkyl, aralkyl, aralkoxy, cycloalkylalkyl, cycloalkylalkoxy, —CN, —$NO_2$, —OH, —$OCF_3$, —$CF_3$, —$NR^4R^5$, —$S(O)_mR^6$, —$S(O)_2NR^4R^5$, —$OS(O)_2R^6$, —$OS(O)_2CF_3$, —$O(CH_2)_xNR^4R^5$, —$C(O)CF_3$, —C(O)alkyl, —C(O)cycloalkyl, —C(O)aralkyl, —C(O)Ar, —$C(O)(CH_2)_xOR^6$, —$C(O)(CH_2)_xNR^4R^5$, —C(O)alkoxy, —$C(O)NR^4R^5$, —$(CH_2)_xC(O)$alkoxy, —$(CH_2)_xOC(O)R^6$, —$(CH_2)_xOR^6$, —$(CH_2)_xR^4R^5$, —$(CH_2)_xC(O)NR^4R^5$, —$(CH_2)_xN(R^4)C(O)R^6$, —$(CH_2)_xS(O)_2NR^4R^5$, —$(CH_2)_xN(R^4)S(O)_2R^6$, —ZAr, —$(CH_2)_xS(O)_2R^6$, —$(OCH_2)_xS(O)_2R^6$, —$N(R^4)S(O)_2R^6$, —$N(R^4)C(O)R^6$, —$(CH_2)_xN(R^4)S(O)_2R^6$, —$(CH^2)_xN(R^4)C(O)R^6$ or —$(CH_2)_xC(O)$alkyl;

$R^4$ and $R^5$ may be the same or different and represent H or alkyl or $R^4$ and $R^5$ together with the atoms to which they are attached form a $C_{3-6}$azacycloalkane, $C_{3-6}$(2-oxo)azacycloalkane ring or $C_{5-8}$ polymethylene chain optionally interrupted by heteroatoms such as O or —$NR^7$.

Z is O, S or $NR^7$;

$R^6$ is alkyl or aryl;

$R^7$ is hydrogen, alkyl or aryl;

m is 1 or 2;

n is 0, 1, 2 or 3;

p and q are independently 0, 1, 2, or 3 or 4;

r is 0 or 1;

s is 0 or 1 such that r+s=1; and x is 0, 1, 2, 3, 4, 5 or 6.

GB Patent Application No. 0305290.9 (Glaxo Group Ltd) discloses compounds of formula (9):

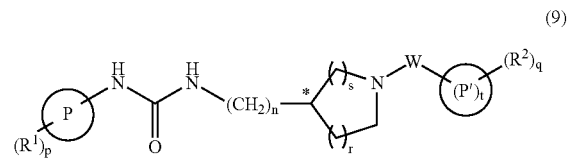

(9)

or a pharmaceutically acceptable salt thereof, or a solvate thereof, wherein:

P and P' are independently selected from aryl and heteroaryl;

$R^1$ and $R^2$ are independently selected from —H, halo, alkyl, alkoxy, cycloalkyl, aralkyl, aralkoxy, cycloalkylalkyl, cycloalkylalkoxy, —CN, —$NO_2$, —OH, —$OCF_3$, —$CF_3$, —$NR^4R^5$, —$S(O)_mR^6$, —$S(O)_2NR^4R^5$, —$OS(O)_2R^6$, —$OS(O)_2CF_3$, —$O(CH_2)_xNR^4R^5$, —$C(O)CF_3$, —C(O)alkyl, —C(O)cycloalkyl, —C(O)aralkyl, —C(O)Ar, —$C(O)(CH_2)_xOR^6$, —$C(O)(CH_2)_xNR^4R^5$, —C(O)alkoxy, —$C(O)NR^4R^5$, —$(CH_2)_xC(O)$alkoxy, —$(CH_2)_xOC(O)R^6$, —$(CH_2)_xOR^6$, —$(CH_2)_xR^4R^5$, —$(CH_2)_xC(O)NR^4R^5$, —$(CH_2)_xN(R^4)C(O)R^6$, —$(CH_2)_xS(O)_2NR^4R^5$, —$(CH_2)_xN(R^4)S(O)_2R^6$, —ZAr, —$(CH_2)_xS(O)_2R^6$, —$(OCH_2)_xS(O)_2R^6$, —$N(R^4)S(O)_2R^6$, —$N(R^4)C(O)R^6$, —$(CH_2)_xN(R^4)S(O)_2R^6$, —$(CH^2)_xN(R^4)C(O)R^6$ or —$(CH_2)_xC(O)$alkyl;

$R^4$ and $R^5$ may be the same or different and represent H or alkyl or $R^4$ and $R^5$ together with the atoms to which they are attached form a $C_{3-6}$azacycloalkane, $C_{3-6}$(2-oxo)azacycloalkane ring or $C_{5-8}$ polymethylene chain optionally interrupted by heteroatoms such as O or —$NR^7$.

Z is O, S or $NR^7$;

W is a group CH or $(CH_2)CH$;

$R^6$ is alkyl or aryl;

$R^7$ is hydrogen, alkyl or aryl;

m is 1 or 2;

n is 0, 1, 2 or 3;

p and q are independently 0, 1, 2, or 3 or 4;

r is 0, 1, 2 or 3;

s is 0, 1 or 2;

t is 1 or 2 and x is 0, 1, 2, 3, 4, 5 or 6.

GB Patent Application No. 0305165.3 (Glaxo Group Ltd) discloses compounds of formula (10):

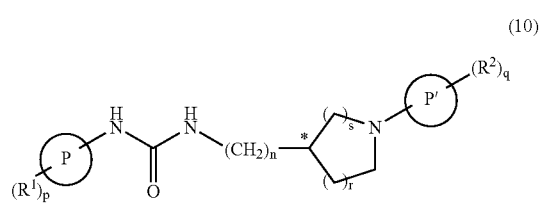

(10)

or a pharmaceutically acceptable salt thereof, or a solvate thereof, wherein:

P is iso-quinolinyl;

P' is selected from phenyl, pyridinyl or pyrimidinyl;

$R^1$ and $R^2$ are independently selected from —H, halo, alkyl, alkoxy, cycloalkyl, aralkyl, aralkoxy, cycloalkylalkyl, cycloalkylalkoxy, —CN, —NO$_2$, —OH, —OCF$_3$, —CF$_3$, —NR$^4$R$^5$, —S(O)$_m$R$^6$, —S(O)$_2$NR$^4$R$^5$, —OS(O)$_2$R$^6$, —OS(O)$_2$CF$_3$, —O(CH$_2$)$_x$NR$^4$R$^5$, —C(O)CF$_3$, —C(O)alkyl, —C(O)cycloalkyl, —C(O)aralkyl, —C(O)Ar, —C(O)(CH$_2$)$_x$OR$^6$, —C(O)(CH$_2$)$_x$NR$^4$R$^5$, —C(O)alkoxy, —C(O)NR$^4$R$^5$, —(CH$_2$)$_x$C(O)alkoxy, —(CH$_2$)$_x$OC(O)R$^6$, —(CH$_2$)$_x$OR$^6$, —(CH$_2$)$_x$R$^4$R$^5$, —(CH$_2$)$_x$C(O)NR$^4$R$^5$, —(CH$_2$)$_x$N(R$^4$)C(O)R$^6$, —(CH$_2$)$_x$S(O)$_2$NR$^4$R$^5$, —(CH$_2$)$_x$N(R$^4$)S(O)$_2$R$^6$, —ZAr, —(CH$_2$)$_x$S(O)$_2$R$^6$, —(OCH$_2$)$_x$S(O)$_2$R$^6$, —N(R$^4$)S(O)$_2$R$^6$, —N(R$^4$)C(O)R$^6$, —(CH$_2$)$_x$N(R$^4$)S(O)$_2$R$^6$, —(CH$^2$)$_x$N(R$^4$)C(O)R$^6$ or —(CH$_2$)$_x$C(O)alkyl;

$R^4$ and $R^5$ may be the same or different and represent H or alkyl or $R^4$ and $R^5$ together with the atoms to which they are attached form a $C_{3-6}$azacycloalkane, $C_{3-6}$(2-oxo)azacycloalkane ring or $C_{5-8}$ polymethylene chain optionally interrupted by heteroatoms such as O or —NR$^7$.

Z is a bond, O, S or NR$^7$;
$R^6$ is alkyl or aryl;
$R^7$ is hydrogen, alkyl or aryl;
m is 1 or 2;
n is 0, 1, 2 or 3;
p and q are independently 0, 1, 2, or 3 or 4;
r is 1, 2 or 3;
s is 0, 1 or 2; and
x is 0, 1, 2, 3, 4, 5 or 6.

GB Patent Application No. 0305426.9 (Glaxo Group Ltd) discloses compounds of formula (11):

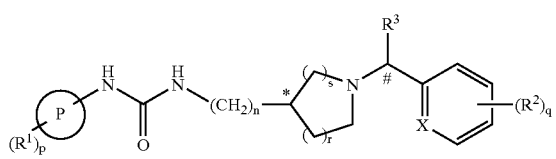

(11)

or a pharmaceutically acceptable salt thereof, or a solvate thereof, wherein:

P is selected from cinnolinyl, phenyl, quinazolinyl, quinolinyl or iso-quinolinyl;
$R^1$ and $R^2$ are independently selected from —H, halo, alkyl, alkoxy, cycloalkyl, aralkyl, aralkoxy, cycloalkylalkyl, cycloalkylalkoxy, —CN, —NO$_2$, —OH, —OCF$_3$, —CF$_3$, or —NR$^4$R$^5$;
$R^3$ is H or alkyl;
$R^4$ and $R^5$ may be the same or different and represent H or alkyl;
n is 0, 1, 2 or 3;
p and q are independently 0, 1, 2, or 3 or 4;
r is 0, 1, 2 or 3;
s is 0, 1 or 2; provided that both r and s are not 0; and
X=C or N.

GB Patent Application No. 0305285.9 (Glaxo Group Ltd) discloses compounds of formula (12):

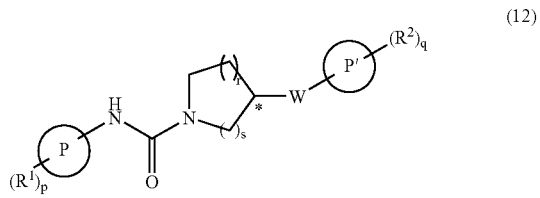

(12)

or a pharmaceutically acceptable salt thereof, or a solvate thereof, wherein:

P and P' are independently selected from aryl and heteroaryl;
$R^1$ and $R^2$ are independently selected from —H, halo, alkyl, alkoxy, cycloalkyl, aralkyl, aralkoxy, cycloalkylalkyl, cycloalkylalkoxy, —CN, —NO$_2$, —OH, —OCF$_3$, —CF$_3$, —NR$^4$R$^5$, —S(O)$_m$R$^6$, —S(O)$_2$NR$^4$R$^5$, —OS(O)$_2$R$^6$, —OS(O)$_2$CF$_3$, —O(CH$_2$)$_x$NR$^4$R$^5$, —C(O)CF$_3$, —C(O)alkyl, —C(O)cycloalkyl, —C(O)aralkyl, —C(O)Ar, —C(O)(CH$_2$)$_x$OR$^6$, —C(O)(CH$_2$)$_x$NR$^4$R$^5$, —C(O)alkoxy, —C(O)NR$^4$R$^5$, —(CH$_2$)$_x$C(O)alkoxy, —(CH$_2$)$_x$OC(O)R$^6$, —(CH$_2$)$_x$OR$^6$, —(CH$_2$)$_x$R$^4$R$^5$, —(CH$_2$)$_x$C(O)NR$^4$R$^5$, —(CH$_2$)$_x$N(R$^4$)C(O)R$^6$, —(CH$_2$)$_x$S(O)$_2$NR$^4$R$^5$, —(CH$_2$)$_x$N(R$^4$)S(O)$_2$R$^6$, —ZAr, —(CH$_2$)$_x$S(O)$_2$R$^6$, —(OCH$_2$)$_x$S(O)$_2$R$^6$, —N(R$^4$)S(O)$_2$R$^6$, —N(R$^4$)C(O)R$^6$, —(CH$_2$)$_x$N(R$^4$)S(O)$_2$R$^6$, —(CH$^2$)$_x$N(R$^4$)C(O)R$^6$ or —(CH$_2$)$_x$C(O)alkyl;

$R^4$ and $R^5$ may be the same or different and represent H or alkyl or $R^4$ and $R^5$ together with the atoms to which they are attached form a $C_{3-6}$azacycloalkane, $C_{3-6}$(2-oxo)azacycloalkane ring or $C_{5-8}$ polymethylene chain optionally interrupted by heteroatoms such as O or —NR$^7$.

Z is O, S or NR$^7$;
W is NR$^7$;
$R^6$ is alkyl or aryl;
$R^7$ is hydrogen, alkyl or aryl;
m is 1 or 2;
p and q are independently 0, 1, 2, or 3 or 4;
r is 1, 2 or 3;
s is 0, 1 or 2; and
x is 0, 1, 2, 3, 4, 5 or 6.

GB Patent Application No. 0305163.8 (Glaxo Group Ltd) discloses compounds of formula (13):

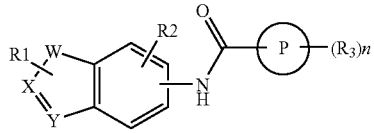

(13)

or a pharmaceutically acceptable salt or solvate thereof, wherein,

P is aryl or heteroaryl;
$R^1$ is —H, alkyl, cycloalkyl, cycloalkylalkyl, aryl, arylalkyl, aryloxyalkyl, —(CH$_2$)$_x$OR$^4$ or —(CH$_2$)$_x$NR$^4$R$^5$;
$R^2$ is —H, alkyl, alkoxy or halo;
$R^3$ is —H, halo, alkyl, alkoxy, cycloalkyl, aryl wherein said aryl group may be optionally substituted by one or more halo atoms; aralkyl, aralkoxy, cycloalkylalkyl, cycloalkylalkoxy, —CN, —NO$_2$, —OH, —OCF$_3$, —NR$^4$R$^5$, —S(O)$_m$R$^6$, —S(O)$_2$NR$^4$R$^5$, —OS(O)$_2$R$^6$, —OS(O)$_2$CF$_3$, —O(CH$_2$)$_x$NR$^4$R$^5$, —O(CH$_2$)$_x$OR$^4$, —C(O)CF$_3$, —C(O)alkyl, —C(O)cycloalkyl, —C(O)

aralkyl, —C(O)Ar, —C(O)(CH₂)ₓOR⁶, —C(O)(CH₂)ₓNR⁴R⁵, —C(O)alkoxy, —C(O)NR⁴R⁵, —(CH₂)ₓC(O)alkoxy, —(CH₂)ₓOC(O)R⁶, —(CH₂)ₓOR⁶, —(CH₂)ₓR⁴R⁵, —(CH₂)ₓC(O)NR⁴R⁵, —(CH₂)ₓN(R⁴)C(O)R⁶, —(CH₂)ₓS(O)₂NR⁴R⁵, —(CH₂)ₓN(R⁴)S(O)₂R⁶, —ZAr, —(CH₂)ₓS(O)₂R⁶, —(OCH₂)ₓS(O)₂R⁶, —N(R⁴)S(O)₂R⁶, —N(R⁴)C(O)R⁶, —(CH₂)ₓN(R⁴)S(O)₂R⁶, —(CH²)ₓN(R⁴)C(O)R⁶ or —(CH₂)ₓC(O)alkyl;

R⁴ and R⁵ may be the same or different and represent —H or alkyl or R⁴ and R⁵ together with the nitrogen atom to which they are attached form a heterocyclic ring;

R⁶ is —H, alkyl or aryl;

Ar is aryl or heteroaryl, x is 0, 1, 2,3,4, 5 or 6;

W, X and Y form a 5-membered nitrogen containing heterocyclic ring;

Z is a bond, O, S, NR⁷ or CH₂; and n is an integer value from 1 to 6.

GB Patent Application No. 0316554.5 (Glaxo Group Ltd) discloses compounds of formula (14):

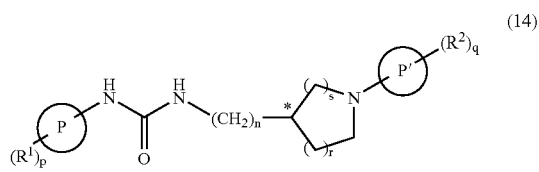

or a pharmaceutically acceptable salt thereof, or a solvate thereof, wherein:

P represents iso-quinolinyl;

P' is selected from phenyl, pyridinyl, pyrimidinyl and thiazolyl;

R¹ and R² are independently selected from —H, halo, alkyl, alkoxy, cycloalkyl, aralkyl, aralkoxy, cycloalkylalkyl, cycloalkylalkoxy, —CN, —NO₂, —OH, —OCF₃, —CF₃, —NR⁴R⁵, —S(O)ₘR⁶, —S(O)₂NR⁴R⁵, —OS(O)₂R⁶, —OS(O)₂CF₃, —O(CH₂)ₓNR⁴R⁵, —C(O)CF₃, —C(O)alkyl, —C(O)cycloalkyl, —C(O)aralkyl, —C(O)Ar, —C(O)(CH₂)ₓOR⁶, —C(O)(CH₂)ₓNR⁴R⁵, —C(O)alkoxy, —C(O)NR⁴R⁵, —(CH₂)ₓC(O)alkoxy, —(CH₂)ₓOC(O)R⁶, —(CH₂)ₓOR⁶, —(CH₂)ₓR⁴R⁵, —(CH₂)ₓC(O)NR⁴R⁵, —(CH₂)ₓN(R⁴)C(O)R⁶, —(CH₂)ₓS(O)₂NR⁴R⁵, —(CH₂)ₓN(R⁴)S(O)₂R⁶, —ZAr, —(CH₂)ₓS(O)₂R⁶, —(OCH₂)ₓS(O)₂R⁶, —N(R⁴)S(O)₂R⁶, —N(R⁴)C(O)R⁶, —(CH₂)ₓN(R⁴)S(O)₂R⁶, —(CH²)ₓN(R⁴)C(O)R⁶ or —(CH₂)ₓC(O)alkyl;

R⁴ and R⁵ may be the same or different and represent H or alkyl or R⁴ and R⁵ together with the atoms to which they are attached form a C₃₋₆azacycloalkane, C₃₋₆(2-oxo)azacycloalkane ring or C₅₋₈ polymethylene chain optionally interrupted by heteroatoms such as O or —NR⁷;

Z represents a bond, O, S or NR⁷;

R⁶ represents alkyl or aryl;

R⁷ represents hydrogen, alkyl or aryl;

m represents an integer 1 or 2;

n represents an integer 0, 1, 2 or 3;

p and q independently represent an integer 0, 1, 2, or 3 or 4;

r represents an integer 1, 2 or 3;

s represents an integer 0, 1 or 2 wherein r+s=2, 3 or 4; and x represents an integer 0, 1, 2, 3, 4, 5 or 6.

International Patent Application WO 02/08221 (Neurogen Corporation US) discloses compounds of formula (15):

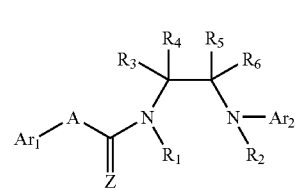

wherein:

A is chosen from O, S, NR_A, CR_BR_B', NR_ACR_BR_B', CR_BR_B'NR_A, —CR_A=CR_B—, and C₃H₄; where R_A, R_B, and R_B' are independently selected at each occurrence from hydrogen or alkyl;

Z is oxygen or sulfur. R₁ and R₂ independently represent hydrogen or lower alkyl; or R₁ and R₂ are taken together to form a 5 to 8 membered nitrogen containing ring of the formula:

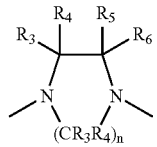

wherein n is 1, 2 or 3;

R₃ and R₄ are independently selected at each occurrence from the group consisting of hydrogen; halogen; hydroxy; amino; cyano; nitro; —COOH; —CHO, optionally substituted alkyl; optionally substituted alkenyl; optionally substituted alkynyl; optionally substituted alkoxy; optionally substituted mono or dialkylamino; optionally substituted alkylthio; optionally substituted alkyl ketone; optionally substituted alkylester, optionally substituted alkylsulfinyl; optionally substituted alkylsufonyl; optionally substituted mono- or di-alkylcarboxamide; optionally substituted —S(O)ₙNHalkyl; optionally substituted —S(O)ₙN{alkyl)(alkyl); optionally substituted —NHC(=O)alkyl; optionally substituted NC(=(O)(alkyl)(alkyl); optionally substituted —NHS(O)ₙalkyl; optionally substituted —NS(O)ₙ(alkyl)(alkyl); optionally substituted saturated or partially unsaturated heterocycloalkyl of from 5 to 8 atoms, which saturated or partially unsaturated heterocycloalkyl contains 1,2, or 3 heteroatoms selected from N, O, and S; optionally substituted aryl having from 1 to 3 rings; or optionally substituted heteroaryl, said heteroaryl having from 1 to 3 rings, 5 to 8 ring members in each ring and, in at least one of said rings, from 1 to about 3 heteroatoms per ring selected from the group consisting of N, O, and S, —or any two R₃ and R₄ not attached to the same carbon may be joined to form an optionally substituted any 1 ring, a saturated or partially unsaturated carbocyclic ring of from 5 to 8 members, which carbocyclic ring is optionally substituted; or a saturated, partially unsaturated, or aromatic heterocyclic ring of from 5 to 8 members, which heterocyclic ring is optionally substituted and contains 1, 2, or 3 heteroatoms selected form N, O, and S; and Ar₁ and Ar₂ are the same or different and independently represent optionally substituted cycloalkyl; an substituted heterocycloalkyl ring of from 5 to 8 atoms, which ring contains 1, 2, or 3 heteroatoms selected from N, O, and S; optionally substituted aryl, having from 1 to 3 rings,—or optionally substituted heteroaryl, said heteroaryl having from 1 to 3 rings, 5 to 8 ring members in each ring and, in at least one of said rings, from 1 to about 3 heteroatoms per ring selected from the group consisting of N, O, and S, and n is independently chosen at each occurrence from 0, 1, and 2.

International Patent Application WO 02/16317 (Pacific Corporation KR) discloses compounds of formula (16):

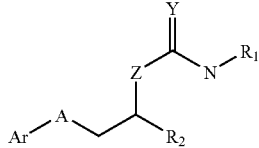

(16)

wherein, $R_1$ represents Ar'—$(CH_2)_m$— (wherein Ar' is phenyl, pyridinyl, thiophenyl or naphthalenyl substituted or unsubstituted with halogen or lower alkyl having 1 to 5 carbon atoms; or trifluoromethylphenyl, and m is 1, 2, 3 or 4), —$(CH_2)_n$—$CHPh_2$, or —$CH_2CH_2CH(Ph)CH_2Ph$ (wherein n is 1 or 2);

Y represents S or O;

Z represents O, —$CH_2$—, NRs, $CHR_3$ (wherein $R_3$ is hydrogen, lower alkyl having 1 to 5 carbon atoms, benzyl or phenethyl);

$R_2$ represents hydrogen, lower alkyl having 1 to 6 carbon atoms, cycloalkyl, dimethyl, or Ar"—$(CH_2)_p$— (wherein Ar" is phenyl substituted or unsubstituted with halogen or trifluoromethyl; or pyridinyl, imidazolyl or indolyl substituted or unsubstituted with carboxyl, amino, methanesulfonylamino or t-butoxycarbonyl, p is 0, 1, 2, 3 or 4);

A represents O or —$CH_2$—; and

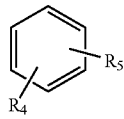

Ar represents (wherein $R_4$ and $R_5$ each independently are hydrogen, hydroxy, methoxy, nitro, cyano, benzyloxy, amino, methanesulfonylamino, halogen, lower alkyl having 1 to 5 carbon atoms, —$NHCO_2CH_3$, —$NHC(=O)CH_3$, trifluoromethyl, sulfamoyl, carboxyl, —$OCH_2OCH_3$, methoxycarbonyl); or pyridinyl, indolyl or imidazolyl substituted or unsubstituted with carboxyl, amino, methanesulfonylamino, phenethylaminocarbonyl or t-butoxycarbonyl.

International Patent Application WO 02/16319 (Pacific Corporation KR) discloses compounds of formula (17):

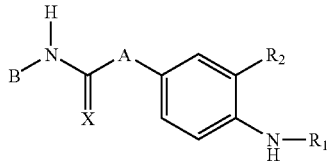

(17)

wherein, X represents a sulfur atom or an oxygen atom;

$R_1$ represents a lower alkyl sulfonyl group having 1 to 5 carbon atoms, an aryl sulfonyl group or a lower alkyl carbonyl group having 1 to 5 carbon atoms, which may be unsubstituted or substituted with halogen atom;

$R_2$ represents a hydrogen atom, a methoxy group or a halogen;

when A is —$NHCH_2$—, B represents

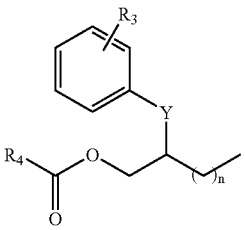

(wherein, n is 0 or 1), or when A is —$CH_2$—, B represents 4-t-butylbenzyl, 3,4-dimethylphenylethyl,

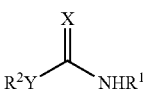

or an oleyl group;

Y represents —$CH_2$— or $CH_2CH_2$—; represents hydrogen atom or a lower alkyl group having 1 to 5 carbon atoms; and $R_4$ represents a lower alkyl group having 1 to 5 carbon atoms or phenyl group.

International Patent Application WO 02/16318 (Pacific Corporation KR) discloses compounds of formula (18):

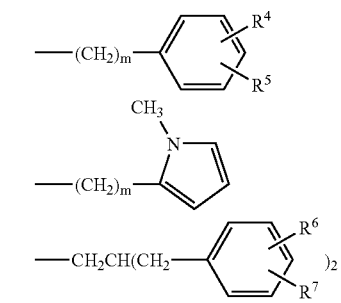

(18)

wherein,

X represents S, O or —NCN;

Y represents single bond, $NR^3$, O or S;

$R^1$ represents pyridinylmethyl, pyrrolylmethyl, oxazolylmethyl, pyrazolylmethyl, imidazolylmethyl, anthracenylmethyl, naphthylmethyl, quinolinylmethyl, alkoxycarbonyl or alkylcarbonyloxy (wherein, m is 0, 1, 2, 3 or 4; $R^4$ and $R^5$ are independently hydrogen, lower alkyl having 1 to 5 carbon atoms, hydroxy, methanesulfonylamino, lower alkoxy having 1 to 5 carbon atoms, methoxyalkoxy, methoxyalkoxyalkyl, alkoxycarbonyloxy, benzyloxy, acetoxymethyl, propinoyloxymethyl, butoxyalkyl, trimethylacetoxy, trimethylacetoxymethyl or halogen; and R and R are independently hydrogen, lower alkyl having 1 to 5 carbon atoms);

$R^2$ represents $R^8CH_2)_n$— {wherein, n is 0, 1, 2, 3 or 4; $R^8$ is benzoyl, imidazolyl, indolyl, indazolyl, thiazolyl, pyrazolyl, oxazolyl, isoxazolyl, benzimidazolyl, chromonyl or benzothiazolyl substituted or unsubstituted with lower alkyl having 1 to 5 carbon atoms, nitro, amino, cyano, methanesulfonylamino, formyl or halogen, or

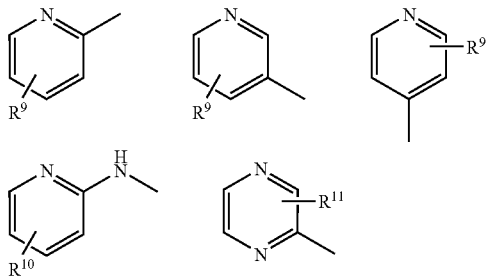

(wherein, $R^9$ is hydrogen, halogen, lower alkyl having 1 to 5 carbon atoms, lower alkoxy having 1 to 5 carbon atoms, hydroxy, nitro, cyano, —$NHSO_2R^{12}$—$S(O)_pR^{12}$, —$NR^{13}R^{14}$, carboxyl; $R^{10}$ is hydrogen, nitro, $NHSO_2R^{12}$, $S(O)^pR^{12}$ or $NR^{13}R^W$; $R^{11}$ is hydrogen or cyano; R is lower alkyl having 1 to 5 carbon atoms, methylphenyl, $NR^{13}R^{14}$, trifluoromethyl or alkenyl; $R^{13}$ and $R^{14}$ are independently hydrogen or lower alkyl having 1 to 5 carbon atoms; and p is 0 or 2); or

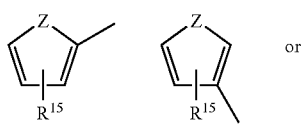

(wherein, Z is O, S, NH or —NCHa; $R^{15}$ is hydrogen, halogen, lower alkyl having 1 to 5 carbon atoms, nitro, cyano, —$NHSO_2R^{12}$, —$S(O)_pR^{12}$, N,N-dimethylaminomethyl or alkoxycarbonylamino; and p and $R^{12}$ have the same meanings as defined in $R^9$); or

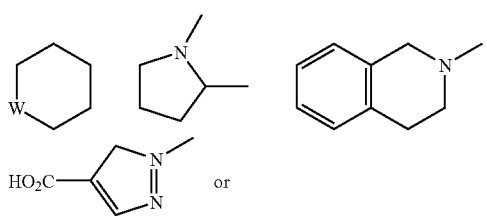

(wherein, W is O, S, NH, $NR^{16}$, —$N(SO_2CH_3)$— or —$CH_2s$ and $R^{16}$ is pyridinyl or pyrimidinyl substituted or unsubstituted with lower alkyl having 1 to 5 carbon atoms, nitro, methanesulfonylamino or halogen; or benzyl or phenethyl substituted or unsubstituted with lower alkyl having 1 to 5 carbon atoms, alkoxy, hydroxy, nitro, methanesulfonylamino or halogen): or

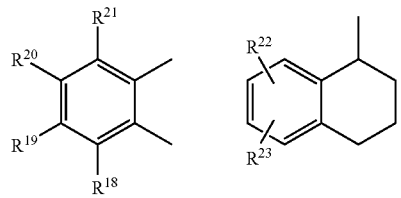

(wherein, $R^{17}$, $R^{18}$, $R^{19}$, $R^{20}$ and $R^{21}$ are independently hydrogen, halogen, lower alkyl having 1 to 5 carbon atoms, alkoxy, methylenedioxy, methanesulfonylaminomethyl, alkoxycarbonyl, hydroxy, sulfamoyl, atninoalkoxy, alkoxycarbonylamino, —$NHCHaCC^{\wedge}H$, alkoxyalkylcarbonylamino, alkoxycarbonylalkylamino, nitro, formyl, acetyl, formylamino, acetoxyamino, cyano, —$OSO_2CH_3$, —$NHSO_2R^{12}$, —$N(SO_2R^{12})CH_3$, —$N(SO_2R^{12})_2$, —$S(O)_pR^{12}$, —$NR^{13}R^{14}$, thiocarbamoyl, —$C(=O)NHNH_2$, —$C(=O)NHOH$, —$C(=O)NHOCH_3$)—$PO(=O)(OCH_3)_2$, carboxyl, NHBoc, —$NHC(=O)SCH_3$ or guanidine; $R^{22}$ and $R^{23}$ are independently hydrogen, halogen, alkoxy or hydroxy; and p, $R^{12}$, $R^{13}$ and $R^{14}$ have the same meanings as defined in $R^9$);

or hydroxyphenylalkyl or (methanesulfonylaminophenyl)alkyl}; and $R^3$ represents hydrogen, alkyl or cycloalkyl having 1 to 8 carbon atoms, lower alkylphenyl having 1 to 5 carbon atoms, pyridinylethyl, bisphenylmethyl; or phenylalkyl substituted with lower alkyl having 1 to 5 carbon atoms, halogen or methanesulfonylamino.

International Patent Application WO 02/30956 (Driver-drugs ES) discloses compounds of formula (19):

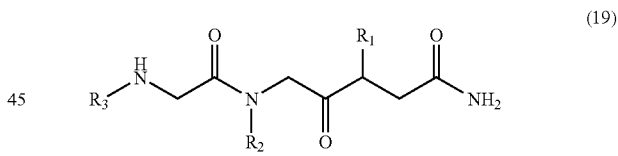

(19)

wherein, $R_1$ represents 2-(2,4-dichlorophenyl)ethyl, 3-methyl-butyl, 2-(methylcarbonylaraino)ethyl, 2-(N-imidazolyl)ethyl or 3-(N,N-dimethylamino)propyl; $R_2$ represents 2-(2,4-dichlomphenylethyl, 2-(4-methoxyphenyl)ethyl, 3,3-diphenylpropyl or 3-(N,N-dielhylamino)propyl and $R_3$ represents N,N-diethyl-aminopropyl, 3,3-diphenyl-propyl or 2-[2-(N-methyl)pyrrolidinyl]ethyl;

and salts and solvates thereof, in particular, physiologically acceptable solvates and salts thereof.

For the avoidance of doubt, when a particular variable, such as $R^1$, is referred to above in respect of more than one specific formula, such as formula (1) and formula (2), the value of said variable is to be read and defined by the particular formula at issue, unless it is specifically stated herein that the variable is to be read and defined in the context of more than one formula.

The above-mentioned compounds are described as having biological activity as VR-1 antagonists, and as such are indicated to be useful in the treatment and/or prophylaxis of VR-1 mediated disorders. In particular such compounds may be useful for the treatment or prophylaxis of disorders such as pain, chronic pain, neuropathic pain, postoperative pain, rheumatoid arthritic pain, osteoarthritic pain, back pain, visceral pain, cancer pain, algesia, neuralgia, migraine, neuropathies, diabetic neuropathy, sciatica, HIV-related neuropathy, post-herpetic neuralgia, fibromyalgia, nerve injury, ischaemia, neurodegeneration, stroke, post stroke pain, multiple sclerosis, respiratory diseases, asthma, cough, COPD, inflammatory disorders, oesophagitis, gastroeosophagal reflux disorder (GERD), irritable bowel syndrome, inflammatory bowel disease, pelvic hypersensitivity, urinary incontinence, cystitis, burns, psoriasis and pruritus.

The above-mentioned patent applications describe in relation to the vanilloid VR-1 antagonists they disclose both suitable methods for their preparation and doses for their administration.

We have now found that administration of certain vanilloid VR-1 antagonists in conjunction with an NSAID, such as a COX-2 inhibitor, surprisingly provides a particularly beneficial effect in the treatment of conditions associated with pain and in alleviating the symptoms associated therewith.

Non-steroidal anti-inflammatory drugs (NSAIDS) are already used for the treatment of conditions associated with pain and in alleviating the symptoms associated therewith. However, significant side effects such as, inter alia, gastrointestinal erosion and renal impairment limit their use. The use of combinations of the present invention is perceived to be particularly beneficial since such combinations allow an increased alleviation of conditions associated with pain and their associated symptoms without exceeding the recommended dosage for NSAIDS.

The combinations of the present invention may also facilitate the attainment of the same level of alleviation of conditions associated with pain and their associated symptoms as higher doses of solely administered NSAIDS by using lower doses of NSAIDS in combination with the VR-1 receptor antagonists and thereby lowering the risk of significant side effects associated with NSAID use.

The combinations of the present invention may suitably comprise a sub-maximal amount of a vanilloid receptor VR-1 antagonist or an NSAID, such as a COX-2 inhibitor. Such compositions are indicated to provide a beneficial effect on pain and the conditions associated therewith.

When used herein the term 'sub-maximal amount' of a vanilloid receptor VR-1 antagonist or an NSAID, such as a COX-2 inhibitor means an amount lower than the appropriate non-combination dose for the active agent in question, as described or referred to in reference texts such as the British National Formulary (BNF), British and US Pharmacopoeias, Remington's Pharmaceutical Sciences (Mack Publishing Co.), Martindale The Extra Pharmacopoeia (London, The Pharmaceutical Press). A suitable sub-maximal dose is less than 100% and typically within the range of from 5-95% of the appropriate non-combination dose for the active agent in question, for example 75%, 80%, 90% or 95% of the appropriate non-combination dose for the active agent in question.

In particular, lowering the dose of the NSAID, such as a COX-2 inhibitor, by the use of a sub-maximal dosage, in the presence of a full dose of a vanilloid receptor VR-1 anatagonist also has the benefit of reducing side effects associated with NSAID use.

Drug efficacy may be assessed by using pain models such as carrageenan model (Guilbaud G. & Kayser V. Pain 28 (1987) 99-107) for acute inflammatory pain, FCA model (Freund's Complete Adjuvant) (Hay et al., Neuroscience Vol 78, No 3 pp 843-850, 1997) for chronic inflammatory pain, or CCl model (Chronic Constriction Injury) (Bennett, G. J. & Xie. Y. K. (1988) Pain, 33: 87-107) for neuropathic pain.

According to one aspect of the invention we therefore provide a method of treating conditions associated with pain and alleviating the symptoms associated therewith which comprises administering to a mammal, including man, a vanilloid VR-1 antagonist or a pharmaceutically acceptable derivative thereof and an NSAID, such as a COX-2 inhibitor or a pharmaceutically acceptable derivative thereof, wherein said VR-1 antagonist or said NSAID may optionally be administered as a sub-maximal amount. Suitably, the VR-1 antagonist or the NSAID is administered as a sub-maximal amount.

It will be appreciated that reference to treatment is intended to include prophylaxis as well as the alleviation of established symptoms.

According to another aspect of the invention we provide the use of a vanilloid VR-1 antagonist or a pharmaceutically acceptable derivative thereof and an NSAID, such as a COX-2 inhibitor, or a pharmaceutically acceptable derivative thereof for the manufacture of a medicament for the treatment of conditions associated with pain and the alleviation of symptoms associated thereof.

The combinations of the invention are useful as analgesics. They are therefore useful in treating or preventing pain. They may be used to improve the condition of a host, typically of a human being, suffering from pain. They may be employed to alleviate pain in a host. Thus, the combinations of the invention may be used as a preemptive analgesic to treat acute pain such as musculoskeletal pain, post operative pain and surgical pain, chronic pain such as chronic inflammatory pain (e.g. rheumatoid arthritis (RA) and osteoarthritis (OA), neuropathic pain (e.g. post herpetic neuralgia (PHN), trigeminal neuralgia, neuropathies associated with diabetes and sympathetically maintained pain) and pain associated with cancer and fibromyalgia. The combinations of the invention may also be used in the treatment or prevention of migraine and/or pain associated with migraine, tension headache and cluster headaches and pain associated with Functional Bowel Disorders (e.g. Irritable Bowel Syndrome), non cardiac chest pain and non ulcer dyspepsia.

Additionally, the combinations of the present invention exhibit analgesic and anti-inflammatory activity and are therefore useful in a number of chronic inflammatory pain conditions such as osteoarthritis, rheumatoid arthritis and neuropathic conditions such as fibromyalgia and PHN.

By pharmaceutically acceptable derivative is meant any pharmaceutically acceptable salt, solvate, ester or amide, or salt or solvate of such ester or amide, of the vanilloid VR-1 antagonist or an NSAID, such as a COX-2 inhibitor, or any other compound which upon administration to the recipient is capable of providing (directly or indirectly) the vanilloid VR-1 antagonist or an NSAID, such as a COX-2 inhibitor, or an active metabolite or residue thereof.

Suitable physiologically acceptable salts according to the invention include acid addition salts formed with inorganic acids such as hydrochlorides, hydrobromides, phosphates and sulphates and with organic acids, for example tatrates, maleates, fumarates, succinates and sulfonates.

Suitable vanilloid receptor (VR-1) antagonists include those compounds disclosed in co-pending GB Patent Applications GB 0303464.2, GB 0305291.7, GB 0305290.9, GB 0305165.3, GB 0305426.9, GB 0305285.9, GB 0305163.8 and GB 0316554.5 (Glaxo Group Ltd); co-pending International Patent Application Number PCT/EP03/10262 (Glaxo Group Ltd); and published International Patent Application, Publication Numbers WO 02/072536, WO 02/090326, WO 03/022809, WO 03/053945 and WO 031068749 (Glaxo Group Ltd), WO 02/08221, WO 03/062209 (Neurogen Corporation US), WO 02/16317, WO 02/16318, WO 02/16319 (Pacific Corporation), WO 02/30956 (Diverdrugs ES), WO 02/076946 (Novartis AG), WO 03/049702 (Amgen Inc), WO 03/070247 (Abbott Laboratories), WO 03/066595, WO 03/074520 (Euro-Celtique S. A.), WO 031014064, WO 03/055484, WO 031095420 (Bayer Aktiengellschaft) and WO 03/080578 (Merck Sharpe & Dohme Limited).

Preferred vanilloid receptor (VR-1) antagonists are (2R)-4-(3-chloropyridin-2-yl)-2-methyl-N-[4-trifluoromethyl) phenyl]piperazine-1-carboxamide (Example 20, WO 02/08221) and N-(2-Bromophenyl)-N'-[((R)-1-(5-trifluoromethyl-2-pyridyl)pyrrolidin-3-yl)]urea (Example 1, WO 03/022809).

The compounds described in the above-mentioned Glaxo Group Ltd Patent Applications and physiologically acceptable salts or solvates thereof may be prepared by the processes described below.

Co-pending Patent Application Publication Number WO 02/072536 describes a general process (A) for the preparation of compounds of formulae (1) to (4), (6), (8) to (12) and (14) or a pharmaceutically acceptable salt or solvate thereof, which process comprises coupling a compound of formula (20):

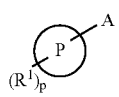
(20)

in which $R^1$, P and p are as defined in formulae (1) to (4), (6), (8) to (11) and (14) with (a) a compound of formula (21):

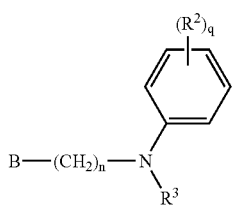
(21)

in which $R^2$, $R^3$, n and q are as defined in formula (1); or (b) a compound of formula (22):

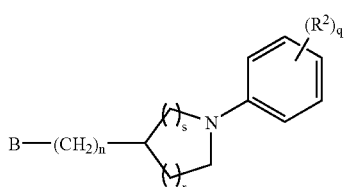
(22)

in which $R^2$, $R^3$, n and q are as defined in formula (2); or (c) a compound of formula (23):

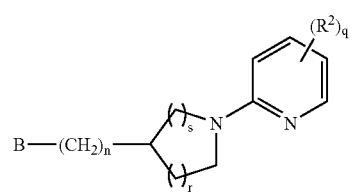
(23)

in which $R^2$, $R^3$, n and q are as defined in formula (3);

(d) a compound of formula (24):

(24)

in which $R^2$, $R^3$, n and q are as defined in formula (4);

(e) a compound of formula (25):

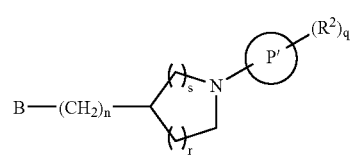
(25)

in which P', $R^2$, n, q, r and s are as defined in formulae (6), (8), (10) and (14);

(f) a compound of formula (26):

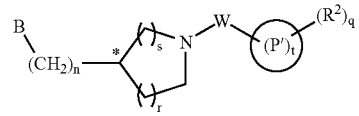
(26)

in which P', $R^2$, W, n, q, r, s and t are as defined in formula (9); or (g) a compound of formula (27):

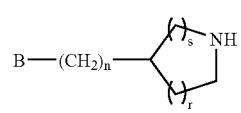
(27)

followed by a compound of formula (28):

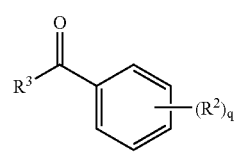
(28)

in which n, r, s q, $R^2$ and $R^3$ are as defined in formula (11); or (h) a compound of formula (29):

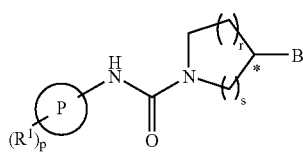
(29)

in which $R^1$, P and p, r, s are as defined in formula (12) and B contains the appropriate functional groups which are capable of forming W;
and A and B contain functional groups which are capable of reacting together to form the urea moiety;
and optionally thereafter if appropriate:
removing any protecting groups;
forming a pharmaceutically acceptable salt of the compound so formed.

Suitable examples of appropriate A and B groups include:
(i) A is —N=C=O and B is $NH_2$; or A is $NH_2$ and B is —N=C=O
(ii) A is $NH_2$ and B is $NH_2$ together with an appropriate urea forming agent.

In process (i) the reaction is carried out in an inert solvent such as dichloromethane or acetonitrile.

In process (ii) the urea forming agent can be carbonyl diimidazole or phosgene, and carried out in an inert organic solvent such as dimethylformamide, tetrahydrofuran or dichloromethane at ambient or elevated temperature in the presence of a base such as triethylamine or pyridine.

An alternative method of synthesis of the unsymmetrical urea compounds of formulae (1) to (4), (6), (8) to (12) and (14) is from a diaryl carbonate, via the corresponding carbamate. Such a methodology is described by Freer et al. (Synthetic Communications, 26(2), 331-349, 1996). It would be appreciated by those skilled in the art that such a methodology could be readily adapted for preparation of the compounds of formulae (1) to (4), (6), (8) to (12) and (14).

A general process for the preparation of a compound of formula (5) or a pharmaceutically acceptable salt or solvate thereof, comprises reacting a compound of formula (30):

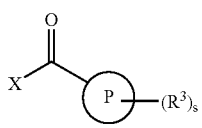
(30)

wherein P, $R^3$ and s are as hereinbefore defined in formula (5), and X is a suitable leaving group, such as a halogen atom or the residue of an activated ester, with a compound of formula (31):

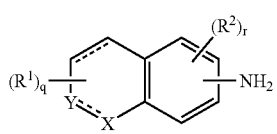
(31)

wherein, $R^1$, $R^2$, q, r, X and Y are as defined in relation to formula (5).

A general process for the preparation of a compound of formula (7) or a pharmaceutically acceptable salt or solvate thereof, comprises reacting a compound of formula (32):

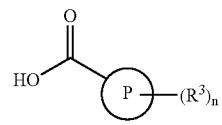
(32)

wherein P, $R^3$ and n are as hereinbefore defined in formula (7), with a compound of formula (33):

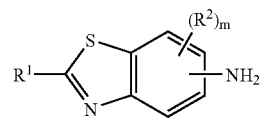
(33)

wherein, $R^1$, $R^2$ and m are as defined in relation to formula (7).

A general process for the preparation of a compound of formula (13) or a pharmaceutically acceptable salt or solvate thereof, comprises reacting a compound of formula (34):

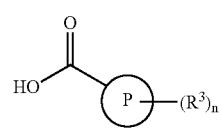
(34)

wherein, P, $R^3$ and n are as defined in relation to formula (13), with a compound of formula (35):

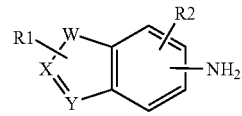
(35)

wherein, $R^1$ and $R^2$ are as defined in relation to formula (13).

The above-mentioned processes for the preparation of compounds of formulae (5), (7) and (13) may be effected using conventional methods for the formation of an amide bond. When X is the residue of an activated ester this may be formed with e.g. a carbodiimide such as 1-ethyl-3-(3-dimethylaminopropyl)carbodiimide. The reaction may be carried out in a solvent such as dichloromethane.

Compounds of formula (31), (33) and (35) may be prepared by reduction of the corresponding nitro-compound. For example, a compound of formula (31) may be prepared by reducing a compound of formula (36):

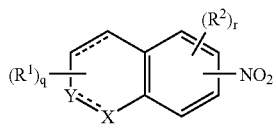

wherein, $R^1$, $R^2$, q and r are as defined in relation to formula (31).

The reduction reaction may be effected by methods well known in the art of catalytic hydrogenation of the nitro-group such as those described in J March, *Advanced Organic Chemistry*, 4th edition, J Wiley & Sons, 1992. A suitable catalyst is 5% palladium on charcoal. The reaction may conveniently be effected in a solvent such as methanol or ethanol.

Compounds of formula (36) may be prepared by reaction of a compound of formula (37),

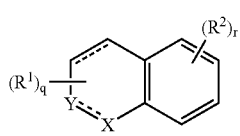

where $R^1$, $R^2$, q and r are as hereinbefore defined for formula (36), with an acylating agent to afford the corresponding amide, followed by reduction. This may be effected by methods well known in the art for (i) acylation of an amine with an acyl chloride, in the presence of a suitable base e.g. triethylamine, in a solvent such as dichloromethane; followed by (ii) reduction of the ketone with borane-tetrahydrofuran complex in a solvent such as tetrahydrofuran.

It will be appreciated by those skilled in the art that it may be necessary to protect certain reactive substituents during some of the above procedures. Standard protection and deprotection techniques, such as those described in Greene T. W. 'Protective groups in organic synthesis', New York, Wiley (1981), can be used. For example, primary amines can be protected as phthalimide, benzyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures known in the art.

Compounds of formulae (20) to (30), (32), (34) and (37) are either commercially available or may be prepared according to known methods or analogous to known methods.

Pharmaceutically acceptable salts may be prepared conventionally by reaction with the appropriate acid or acid derivative.

In a preferred aspect of the invention there is provided a method of treating conditions associated with pain and alleviating the symptoms associated therewith which comprises administering to a mammal, including man, N-(2-Bromophenyl)-N'-[((R)-1-(5-trifluoromethyl-2-pyridyl)pyrrolidin-3-yl)]urea or a pharmaceutically acceptable derivative thereof and an NSAID, such as a COX-2 inhibitor, or a pharmaceutically acceptable derivative thereof.

Suitable NSAIDS for use according to the invention include: naproxen, fenbufen, fenoprofen, flurbiprofen, ketoprofen, dexketoprofen, tiaprofenic acid, azapropazone, diclofenac aceclofenac, diflunisal, indomethacin, ketorolac, mefenamic acid, nabumetone, phenylbutazone, piroxicam, sulindac, tenoxicam, tolfenamic acid, oxaprozin, ibuprofen and COX-2 selective inhibiting compounds (herein referred to as "COX-2 inhibitors").

It will be appreciated that the present invention relates to the use of a vanilloid VR-1 antagonist particularly in conjunction with any compound having COX-2 inhibitor activity known in the art.

A variety of COX-2 inhibitors have been described in the art, for example those mentioned in the following patent applications:

| | | | | |
|---|---|---|---|---|
| AU9719132 | CA2164559 | CA2180624 | EP-799823 | EP-846689 |
| EP-863134 | FR2751966 | GB2283745 | GB2319772 | GB2320715 |
| JP08157361 | US5510368 | US5681842 | US5686460 | US5776967 |
| US5783597 | US5824699 | US5830911 | US5859036 | US5869524 |
| WO94/13635 | WO94/20480 | WO94/26731 | WO95/00501 | WO952/1817 |
| WO96/03385 | WO96/03387 | WO96/06840 | WO96/09293 | WO96/09304 |
| WO96/13483 | WO96/16934 | WO96/19462 | WO96/19463 | WO96/19469 |
| WO96/21667 | WO96/23786 | WO96/24584 | WO96/24585 | WO96/25405 |
| WO96/26921 | WO96/31509 | WO96/36617 | WO96/36623 | WO96/37467 |
| WO96/37469 | WO96/38418 | WO96/38442 | WO96/40143 | WO97/03953 |
| WO97/09977 | WO97/13755 | WO97/13767 | WO97/14691 | WO97/16435 |
| WO97/25045 | WO97/25046 | WO97/25047 | WO97/25048 | WO97/27181 |
| WO97/28120 | WO97/28121 | WO97/30030 | WO97/34882 | WO97/36863 |
| WO97/37984 | WO97/38986 | WO97/40012 | WO97/46524 | WO97/46532 |
| WO98/03484 | WO98/04527 | WO98/06708 | WO98/06715 | WO98/07425 |
| WO98/11080 | WO98/15528 | WO98/21195 | WO98/22442 | WO98/28292 |
| WO98/29382 | WO98/41511 | WO98/41516 | WO98/43966 | WO98/45294 |
| WO98/46594 | WO98/46611 | WO98/47890 | WO98/51667 | WO98/57924 |
| WO99/01455 | WO99/05104 | WO99/10331 | WO99/10332 | WO99/11605 |
| WO99/12930 | WO99/14194 | WO99/14195 | WO99/14205 | WO99/15505 |
| ZA9704806 | ZA9802828 | | | | all incorporated herein by reference as if set forth fully herein. The above applications also describe, in relation to the COX-2 inhibitors they disclose, both suitable methods for their preparation and doses for their administration. Suitable COX-2 inhibitors for use according to the invention include: 2-(4-ethoxy-phenyl)-3-(4-methanesulfonyl-phenyl)-pyrazolo[1,5-b]pyridazine, CDC-501, celecoxib, COX-189, 4-(2-oxo-3-phenyl-2,3-dihydrooxazol4-yl)benzenesulfonamide, CS-179, CS-502, D-1367, darbufelone, DFP, DRF4367, etodolac, flosulide, JTE-522 (4-(4-cyclohexyl-2-methyl-5-oxazolyl)-2-fluorobenzenesulfonamide), L-745337, L-768277, L-776967, L-783003, L-791456, L-804600, meloxicam, MK663 (etoricoxib), nimesulide, NS-398, parecoxib, 1-Methylsulfonyl-4-(1,1-dimethyl-4-(4-fluorophenyl)cyclopenta-2,4-dien-3-yl)benzene, 4-(1,5-Dihydro-6-fluoro-7-methoxy-3-(trifluoromethyl)-(2)-benzothiopyrano(4,3-c)pyrazol-1-yl)benzenesulfonamide, 4,4-dimethyl-2-phenyl-3-(4-methylsulfonyl)phenyl)cyclobutenone, 4-Amino-N-(4-(2-fluoro-5-trifluoromethyl)-thiazol-2-yl)-benzene sulfonamide, 1-(7-tert-butyl-2,3-dihydro-3,3-dimethyl-5-benzo-furanyl)-4-cyclopropyl butan-1-one, Pharmaprojects No. 6089 (Kotobuki Pharmaceutical), rofecoxib, RS-113472, RWJ-63556, S-2474, S-33516, SC-299, SC-5755, valdecoxib, UR-8877, UR-8813, UR-8880.

Preferred COX-2 inhibitors for use according to the invention include: celecoxib, rofecoxib, valdecoxib, parecoxib, 4-(4-cyclohexyl-2-methyl-5-oxazolyl)-2-fluorobenzenesulfonamide (JTE-522), MK663, nimesulide, flosulide, DFP and 2-(4-ethoxy-phenyl)3-(4-methanesulfonyl-phenyl)-pyrazolo[1,5-b]pyridazine, and their physiologically acceptable salts or solvates.

More preferred COX-2 inhibitors for use according to the invention are celecoxib, rofecoxib, valdecoxib, parecoxib, 4-(4-cyclohexyl-2-methyl-5-oxazolyl)-2-fluorobenzenesulfonamide (JTE-522) and 2-(4-ethoxy-phenyl)-3-(4-methanesulfonyl-phenyl)-pyrazolo[1,5-b]pyridazine, and their physiologically acceptable salts or solvates.

A particularly preferred COX-2 inhibitor for use according to the invention is 2-(4-ethoxy-phenyl 3-(4-methanesulfonyl-phenyl)-pyrazolo[1,5-b]pyridazine and its physiologically acceptable salts or solvates. Particularly interesting as pharmaceutically acceptable derivatives are modified at the benzenesulfonamide function to provide metabolically labile benzenesulfonamides. Acylated benzenesulphonamide derivatives are of especial interest.

A further particularly preferred COX-2 inhibitor for use according to the invention is rofecoxib and its physiologically acceptable salts or solvates.

According to a further aspect of the invention there is provided a method of treating conditions associated with pain and alleviating the symptoms associated therewith which comprises administering to a mammal, including man a vanilloid VR-1 antagonist or a pharmaceutically acceptable derivative thereof and celecoxib, rofecoxib, valdecoxib, parecoxib, 4-(4-cyclohexyl-2-methyl-5-oxazolyl)-2-fluorobenzenesulfonamide (JTE-522) and 2-(4-ethoxy-phenyl)-3-(4-methanesulfonyl-phenyl)-pyrazolo[1,5-b]pyridazine, or a pharmaceutically acceptable derivative thereof.

A particular preferred combination of the invention is N-(2-Bromophenyl)-N'-[((R)-1-(5-trifluoromethyl-2-pyridyl)pyrrolidin-3-yl)] or a pharmaceutically acceptable derivative thereof and rofecoxib or a pharmaceutically acceptable derivative thereof.

A further particular preferred combination of the invention is N-(2-Bromophenyl)-N'-[((R)-1-(5-trifluoromethyl-2-pyridyl)pyrrolidin-3-yl)] or a pharmaceutically acceptable derivative thereof and 2-(4-ethoxy-phenyl)-3-(4-methanesulfonyl-phenyl)-pyrazolo[1,5-b]pyridazine or a pharmaceutically acceptable derivative thereof.

Compounds for use according to the invention may be administered simultaneously or sequentially and, when administration is sequential, either the vanilloid VR-1 antagonist or the NSAID, such as a COX-2 inhibitor, may be administered first. When administration is simultaneous, the combination may be administered either in the same or different pharmaceutical composition.

Compounds for use according to the invention may be administered as the raw material but the active ingredients are preferably provided in the form of pharmaceutical formulations.

The active ingredients may be used either as separate formulations or as a single combined formulation. When combined in the same formulation it will be appreciated that the two compounds must be stable and compatible with each other and the other components of the formulation. Therefore, pharmaceutical formulations comprising a combination as defined above together with a pharmaceutically acceptable diluent or carrier comprise a further aspect of the invention. When formulated separately they may be provided in any convenient formulation, conveniently in such manner as are known for such compounds in the art.

Accordingly in a further aspect of the invention we provide a pharmaceutical composition which comprises a vanilloid VR-1 antagonist or a pharmaceutically acceptable derivative thereof and an NSAID, such as a COX-2 inhibitor, or a pharmaceutically acceptable derivative thereof formulated for administration by any convenient route, with the proviso that said VR-1 antagonist is not a compound disclosed in International Patent Application, Publication Number WO 02/076946. Such compositions are preferably in a form adapted for use in medicine, in particular human medicine, and can conveniently be formulated in conventional manner using one or more pharmaceutically acceptable carriers or excipients.

There is further provided a pharmaceutical composition which comprises a vanilloid VR-1 antagonist or a pharmaceutically acceptable derivative thereof, an NSAID or a pharmaceutically acceptable derivative thereof and a pharmaceutically acceptbale carrier therefor, with the proviso that said VR-1 antagonist is not a compound disclosed in International Patent Application, Publication Number WO 02/076946.

The above mentioned published documents, including patent applications and patents, are incorporated herein by reference as if each individual publication was specifically and fully set forth herein.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) or in a form suitable for administration by inhalation or insufflation administration, although the most suitable route may depend upon for example the condition and disorder of the recipient. The formulations may conveniently be presented in unit dosage form and may be prepared by any of the methods well known in the art of pharmacy. All methods include the step of bringing into association the compounds ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation. Preferably such compositions will be formulated for oral administration. It will be appreciated that when the two active ingredients are administered independently, each may be administered by different means.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a other conventional excipients such as binding agents, (for example, syrup, acacia, gelatin, sorbitol, tragacanth, mucilage of starch, polyvinylpyrrolidone) or hydroxymethyl cellulose or hydroxymethyl cellulose fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

For topical administration to the epidermis, the compounds may be formulated as creams, gels, ointments or lotions or as a transdermal patch.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For intranasal administration the compounds of the invention may be used, for example as a liquid spray, as a powder or in the form of drops.

For administration by inhalation the compounds according to the invention are conveniently delivered in the form of an aerosol spray presentation from pressurised packs or a nebuliser, with the use of a suitable propellant, e.g. 1,1,1,2-trifluoroethane (HFA 134A) and 1,1,1,2,3,3,3,-heptapropane (HFA 227), carbon dioxide or other suitable gas. In the case of a pressurised aerosol the dosage until may be determined by providing a valve to deliver a metered amount. Capsules and cartridges of e.g. gelatin for use in an inhaler or insufflator may be formulated containing a powder mix of a compound of the invention and a suitable powder base such as lactose or starch.

In addition to the ingredients particularly mentioned above, the formulations may include other agents conventional in the art having regard to the type of formulation in question, for example those suitable for oral administration may include flavouring agents.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02-5000 mg per day, preferably 1-1500 mg per day. The desired dose may conveniently be presented in a single dose or as divided doses administered at appropriate intervals, for example as two, three, four or more sub-doses per day. The formulations according to the invention may contain between 0.1-99% of the active ingredient, conveniently from 30-95% for tablets and capsules and 3-50% for liquid preparations.

Pharmaceutical compositions according to the invention may be prepared by conventional techniques. When combined in the same formulation for example, the vanilloid VR-1 antagonist or a pharmaceutically acceptable derivative thereof and an NSAID, such as a COX-2 inhibitor, or a pharmaceutically acceptable derivative thereof may be admixed together, if desired, with suitable excipients. Tablets may be prepared, for example, by direct compression of such a mixture. Capsules may be prepared, for example by filling the blend together with suitable excipients into gelatin capsules, using a suitable filling machine.

Compositions for use according to the invention may, if desired, be presented in a pack or dispenser device which may contain one or more unit dosage forms containing the active ingredients. The pack may, for example, comprise metal or plastic foil, such as a blister pack. Where the compounds are intended for administration as two separate compositions these may be presented, for example, in the form of a twin pack.

Pharmaceutical compositions may also be prescribed to the patient in "patient packs" containing the whole course of treatment in a single package, usually a blister pack. Patient packs have an advantage over traditional prescriptions, where a pharmacists divides a patients supply of a pharmaceutical from a bulk supply, in that the patient always has access to the package insert contained in the patient pack, normally missing in traditional prescriptions. The inclusion of a package insert has been shown to improve patient compliance with the physicians instructions.

It will be understood that the administration of the combination of the invention by means of a single patient pack, or patients packs of each composition, including a package insert directing the patient to the correct use of the invention is a desirable additional feature of this invention.

According to a further aspect of the invention there is provided a patient pack comprising at least one active ingredient, of the combination according to the invention and an information insert containing directions on the use of the combination of the invention.

According to another aspect the invention provides a double pack comprising in association for separate administration of a vanilloid VR-1 antagonist or pharmaceutically acceptable derivative thereof and an NSAID, such as a COX-2 inhibitor, or pharmaceutically acceptable derivative thereof.

It will be appreciated that the dose at which the vanilloid VR-1 antagonist and the COX-2 inhibitor is administered will depend on the age and condition of the patient and the frequency and route of administration and will be at the ultimate discretion of the attendant physician. The active ingredients may conveniently be presented in unit dose form.

A proposed dose of vanilloid VR-1 antagonist and an NSAID, such as a COX-2 inhibitor, for administration to man (of approximately 70 kg body weight) may conveniently be administered at doses within the normal range taught in the art at which the compounds are therapeutically effective.

For example, a proposed dose of the vanilloid VR-1 antagonist for use according to the invention is 0.1 mg to 2 g, preferably 1 mg to 2 g, more preferably 1 mg to 100 mg per unit dose, expressed as the weight of free base. The unit dose may be administered in single or divided doses, for example, from 1 to 4 times per day.

For example, a proposed dose of the NSAID, such as a COX-2 inhibitor, for use according to the invention is 0.001 to 500 mg, preferably 0.01 to 100 mg, most preferably 0.05 to 50 mg, for example 0.5 to 25 mg per unit dose, expressed as the weight of the free base. The unit dose may be administered in single or divided doses, for example, from 1 to 4 times per day.

DESCRIPTIONS AND EXAMPLE

Description 1 (D1)

[(R)-1-(5-Trifluoromethylpyridin-2-yl)-pyrrolidin-3-yl]-carbamic acid tert-butyl ester To a solution of 2-chloro-5-trifluoromethylpyridine (7.3 g, 0.04 mol) and 3R-(+)-3-(tert-butyloxycarbonylamino)pyrrolidine (7.5 g, 0.04 mol) in dry dimethylformamide (100 ml) was added powdered potassium carbonate (6.6 g, 0.05 mol) and the reaction heated at 100° C. for 7 h and cooled. Solvent was removed under reduced pressure and the residue partitioned between ethyl acetate and water. The organic phase was separated, dried ($MgSO_4$) and filtered. Removal of solvent under reduced pressure gave a solid. Chromatography on silica gel eluting with ethyl acetate and DCM (gradient elution, 20% maximum) afforded the title compound as a white solid (11.5 g, 90%).

Description 2 (D2)

(R)-1-(5-Trifluoromethylpyridin-2-yl)-3-aminopyrrolidine

A solution of D1 (11.5 g, 0.04 mol) in DCM (80 ml) was cooled (ice-bath) and trifluoroacetic acid (excess, 50 ml) was added. Reaction was warmed to ambient temperature, stirred for 3 h and partitioned between ethyl acetate and aqueous sodium hydroxide. The organic phase was separated, dried ($MgSO_4$) and filtered. Removal of solvent under reduced pressure afforded the crude product as a yellow oil. Bulb to bulb distillation under reduced pressure initially afforded the product as a oil which crystallised on standing (6.8 g, 78%).

Example 1

N-(2-Bromophenyl)-N'-[((R)-1-(5-trifluoromethyl-2-pyridyl)pyrrolidin-3-yl)]urea (E1)

To a solution of D2 (0.88 g, 4 mmol) in diethyl ether (30 ml) was added 2-bromophenyl isocyanate (0.8 g, 4 mmol) and the mixture stirred at ambient temperature for 2 h. The precipitated solid was filtered off, washed with ether and dried to afford the title compound as a white solid (1.4 g, 84%).

$^1$H NMR (250 MHz, $d_6$-DMSO) δ 8.41 (s, 1H), 8.10 (d, 1H), 7.78 (m, 2H), 7.54 (d, 1H), 7.46 (d, 1H), 7.28 (m, 1H), 6.89 (m, 1H), 6.62 (d, 1H) 4.34 (m, 1H), 3.69 (m, 1H), 3.56 (m, 2H), 3.40 (m, 1H), 2.25 (m, 1H), 1.96 (m, 1H). MH$^+$ 429, 431.

Biological Data (a) Guinea Pig FCA Model

N-(2-Bromophenyl)N'-[((R)-1-(5-trifluoromethyl-2-pyridyl)pyrrolidin-3-yl)]urea and rofecoxib 100 μl of 1 mg/ml FCA was injected intraplantar into the left paw of 6 groups of 6 male Dunkin-Hartley guinea-pigs (average weight 330 g) in order to induce inflammation and evoke a mechanical hypersensitivity (Ref. Stein, C., Millan, M. J., and Herz, A., Unilateral inflammation of the hind paw in rats as a model of prolonged noxious stimulation: alterations in behaviour and nociceptive thresholds, Pharmacol. Biochem. Behav., 31 (1988) 445-451). 24 hours later 1.5 mg/kg rofecoxib, 1 mg/kg N-(2-Bromophenyl)-N'-[((R)-1-(5-trifluoromethyl-2-pyridyl)pyrrolidin-3-yl)]urea and a combination of both was administered orally with the vehicle being 1% methylcellulose, the dosing volume being 2 ml/kg and dosing straight into the stomach. The methylcellulose was added gradually to the compound into the pestle and mortar and ground together. The mixtures were then sonnicated for 20 minutes. Behavioural readouts of mechanical hyperalgesia were obtained before FCA adminsitration (naive reading), after FCA but before drug administration (pre-dose reading) and 1 hour after drug administration. The readout used was paw pressure The readout used was paw withdrawal in response to paw pressure (Ref. Randall L O, Selitto J J. (1957) A method for measurement of analgesic activity on inflammed tissue. Arch Int. Pharmacodyn 61, 409419.) and the end point was paw withdrawal. The paw pressure equipment also had one silver disc placed on the point to increase the markings by a factor of 2.

Results:

Table 1 shows % inhibition of FCA-induced mechanical hypersensitivity.

TABLE 1

| Treatment | % reversal of mechanical hypersensitivity | SEM |
|---|---|---|
| Vehicle | 10.3 | 3.4 |
| Compound A | 30.6 | 4.5 |
| Compound B | 32.5 | 4.0 |
| Compound A + B | 51.8 | 6.9 |

(Compound A = 1.5 mg/kg rofecoxib; Compound B = 1 mg/kg Example 1)

The invention claimed is:

1. A method of treating pain in a mammal comprising administering to the mammal a VR-1 agonist in conjunction with an NSAID, wherein the VR-1 agonist is 1) N-(2-Bromophenyl)-N'-[((R)-1-(5-trifluoromethyl-2-pyridyl)pyrrolidin-3-yl)]urea or a pharmaceutically acceptable salt thereof; and 2) the NSAID is rofecoxib or a pharmaceutically acceptable salt thereof.

2. The method of claim 1 wherein the VR-1 agonist and the NSAID are each administered in a sub-maximal amount.

* * * * *